(12) United States Patent
Delaloye et al.

(10) Patent No.: US 11,957,573 B2
(45) Date of Patent: Apr. 16, 2024

(54) RELATING TO TRANSCATHETER STENT-VALVES

(71) Applicant: BOSTON SCIENTIFIC LIMITED, Hamilton (BM)

(72) Inventors: Stephane Delaloye, Bulach (CH); Jacques Essinger, StudenbuhleStrasse (CH); Jean-Luc Hefti, Cheseaux-Noréaz (CH); Youssef Biadillah, Munich (DE); Luc Mantanus, Renens (CH); Fabien Lombardi, Prilly (CH)

(73) Assignee: Boston Scientific Medical Device Limited, Galway (IE)

( * ) Notice: Subject to any disclaimer, the term of this patent is extended or adjusted under 35 U.S.C. 154(b) by 220 days.

(21) Appl. No.: 17/323,452

(22) Filed: May 18, 2021

(65) Prior Publication Data
US 2021/0322159 A1 Oct. 21, 2021

Related U.S. Application Data

(63) Continuation of application No. 15/344,135, filed on Nov. 4, 2016, now Pat. No. 11,207,176, which is a (Continued)

(30) Foreign Application Priority Data

Mar. 22, 2012 (EP) ..................................... 12002015

(51) Int. Cl.
*A61F 2/24* (2006.01)
*A61F 2/848* (2013.01)

(52) U.S. Cl.
CPC .......... *A61F 2/2418* (2013.01); *A61F 2/2409* (2013.01); *A61F 2/2412* (2013.01);
(Continued)

(58) Field of Classification Search
None
See application file for complete search history.

(56) References Cited

U.S. PATENT DOCUMENTS

| 3,755,823 A | 9/1973 | Hancock |
| 4,106,129 A | 8/1978 | Carpentier et al. |

(Continued)

FOREIGN PATENT DOCUMENTS

| AU | 20063288896 A1 | 6/2007 |
| AU | 2007294199 A1 | 3/2008 |

(Continued)

*Primary Examiner* — Ann Schillinger
(74) *Attorney, Agent, or Firm* — Seager, Tufte & Wickhem LLP

(57) ABSTRACT

Some embodiments of the present disclosure provide a stent-valve for transcatheter implantation to replace a cardiac valve. In some embodiments, the stent valve being compressible to a compressed state for delivery, and expandable to an operative state for implantation. In some embodiments, the stent-valve comprises a stent, a plurality of leaflets for defining a prosthetic valve, an inner skirt, an outer skirt, and a paravalve seal for sealing against surrounding tissue. In some embodiments, the paravalve seal comprising material that swells in response to contact with blood or components thereof.

17 Claims, 12 Drawing Sheets

Related U.S. Application Data continuation of application No. 14/879,482, filed on Oct. 9, 2015, now abandoned, which is a continuation of application No. 13/839,357, filed on Mar. 15, 2013, now abandoned.

(52) U.S. Cl.
CPC .... *A61F 2/2469* (2013.01); *A61F 2210/0061* (2013.01); *A61F 2220/0075* (2013.01); *A61F 2250/0003* (2013.01); *A61F 2250/0069* (2013.01)

(56) References Cited

U.S. PATENT DOCUMENTS

| | | |
|---|---|---|
| 4,470,157 A | 9/1984 | Love |
| 5,078,720 A | 1/1992 | Burton et al. |
| 5,163,955 A | 11/1992 | Love et al. |
| 5,192,301 A | 3/1993 | Kamiya et al. |
| 5,344,442 A | 9/1994 | Deac |
| 5,354,330 A | 10/1994 | Hanson et al. |
| 5,411,552 A | 5/1995 | Andersen et al. |
| 5,480,424 A | 1/1996 | Cox |
| 5,499,995 A | 3/1996 | Teirstein |
| 5,500,015 A | 3/1996 | Deac |
| 5,540,712 A | 7/1996 | Kleshinski et al. |
| 5,571,174 A | 11/1996 | Love et al. |
| 5,609,626 A | 3/1997 | Quijano et al. |
| 5,653,749 A | 8/1997 | Love et al. |
| 5,662,703 A | 9/1997 | Yurek et al. |
| 5,713,950 A | 2/1998 | Cox |
| 5,713,951 A | 2/1998 | Garrison et al. |
| 5,718,725 A | 2/1998 | Sterman et al. |
| 5,769,882 A | 6/1998 | Fogarty et al. |
| 5,797,960 A | 8/1998 | Stevens et al. |
| 5,807,327 A | 9/1998 | Green et al. |
| 5,817,126 A | 10/1998 | Imran |
| 5,823,956 A | 10/1998 | Roth et al. |
| 5,824,041 A | 10/1998 | Lenker et al. |
| 5,840,081 A | 11/1998 | Andersen et al. |
| 5,855,600 A | 1/1999 | Alt |
| 5,855,601 A | 1/1999 | Bessler et al. |
| 5,861,028 A | 1/1999 | Angell |
| 5,924,424 A | 7/1999 | Stevens et al. |
| 5,938,697 A | 8/1999 | Killion et al. |
| 5,957,949 A | 9/1999 | Leonhardt et al. |
| 5,976,174 A | 11/1999 | Ruiz |
| 5,980,533 A | 11/1999 | Holman |
| 6,029,671 A | 2/2000 | Stevens et al. |
| 6,083,257 A | 7/2000 | Taylor et al. |
| 6,102,944 A | 8/2000 | Huynh et al. |
| 6,110,201 A | 8/2000 | Quijano et al. |
| 6,168,614 B1 | 1/2001 | Andersen et al. |
| 6,171,335 B1 | 1/2001 | Wheatley et al. |
| 6,183,481 B1 | 2/2001 | Lee et al. |
| 6,196,230 B1 | 3/2001 | Hall et al. |
| 6,214,036 B1 | 4/2001 | Letendre et al. |
| 6,254,564 B1 | 7/2001 | Wilk et al. |
| 6,287,334 B1 | 9/2001 | Moll et al. |
| 6,287,339 B1 | 9/2001 | Vazquez et al. |
| 6,331,189 B1 | 12/2001 | Wolinsky et al. |
| 6,350,278 B1 | 2/2002 | Lenker et al. |
| 6,379,383 B1 | 4/2002 | Palmaz et al. |
| 6,401,720 B1 | 6/2002 | Tu et al. |
| 6,406,493 B1 | 6/2002 | Tu et al. |
| 6,409,759 B1 | 6/2002 | Peredo |
| 6,454,799 B1 | 9/2002 | Schreck |
| 6,458,153 B1 | 10/2002 | Bailey et al. |
| 6,530,952 B2 | 3/2003 | Vesely |
| 6,533,807 B2 | 3/2003 | Wolinsky et al. |
| 6,537,310 B1 | 3/2003 | Palmaz et al. |
| 6,562,069 B2 | 5/2003 | Cai et al. |
| 6,569,196 B1 | 5/2003 | Vesely |
| 6,572,652 B2 | 6/2003 | Shaknovich |
| 6,582,462 B1 | 6/2003 | Andersen et al. |
| 6,589,279 B1 | 7/2003 | Anderson et al. |
| 6,613,079 B1 | 9/2003 | Wolinsky et al. |
| 6,635,085 B1 | 10/2003 | Caffey et al. |
| 6,652,555 B1 | 11/2003 | VanTassel et al. |
| 6,682,558 B2 | 1/2004 | Tu et al. |
| 6,682,559 B2 | 1/2004 | Myers et al. |
| 6,695,865 B2 | 2/2004 | Boyle et al. |
| 6,719,787 B2 | 4/2004 | Cox |
| 6,729,356 B1 | 5/2004 | Baker et al. |
| 6,730,118 B2 | 5/2004 | Spenser et al. |
| 6,733,525 B2 | 5/2004 | Yang et al. |
| 6,736,827 B1 | 5/2004 | McAndrew et al. |
| 6,755,855 B2 | 6/2004 | Yurek et al. |
| 6,767,362 B2 | 7/2004 | Schreck |
| 6,790,229 B1 | 9/2004 | Berreklouw |
| 6,805,711 B2 | 10/2004 | Quijano et al. |
| 6,830,584 B1 | 12/2004 | Seguin |
| 6,830,585 B1 | 12/2004 | Artof et al. |
| 6,830,586 B2 | 12/2004 | Quijano et al. |
| 6,849,085 B2 | 2/2005 | Marton |
| 6,875,231 B2 | 4/2005 | Anduiza et al. |
| 6,893,460 B2 | 5/2005 | Spenser et al. |
| 6,908,481 B2 | 6/2005 | Cribier |
| 6,936,066 B2 | 8/2005 | Palmaz et al. |
| 6,942,682 B2 | 9/2005 | Vrba et al. |
| 7,018,406 B2 | 3/2006 | Seguin et al. |
| 7,025,773 B2 | 4/2006 | Gittings et al. |
| 7,025,780 B2 | 4/2006 | Gabbay |
| 7,041,132 B2 | 5/2006 | Quijano et al. |
| 7,044,966 B2 | 5/2006 | Svanidze et al. |
| 7,101,396 B2 | 9/2006 | Artof et al. |
| 7,141,064 B2 | 11/2006 | Scott et al. |
| 7,179,290 B2 | 2/2007 | Cao |
| 7,195,641 B2 | 3/2007 | Palmaz et al. |
| 7,198,646 B2 | 4/2007 | Figulla et al. |
| 7,201,772 B2 | 4/2007 | Schwammenthal et al. |
| 7,217,287 B2 | 5/2007 | Wilson et al. |
| 7,252,682 B2 | 8/2007 | Seguin |
| 7,276,078 B2 | 10/2007 | Spenser et al. |
| 7,285,130 B2 | 10/2007 | Austin |
| 7,316,712 B2 | 1/2008 | Peredo |
| 7,318,278 B2 | 1/2008 | Zhang et al. |
| 7,320,704 B2 | 1/2008 | Lashinski et al. |
| 7,320,705 B2 | 1/2008 | Quintessenza |
| 7,329,278 B2 | 2/2008 | Seguin et al. |
| 7,329,279 B2 | 2/2008 | Haug et al. |
| 7,331,991 B2 | 2/2008 | Kheradvar et al. |
| 7,331,993 B2 | 2/2008 | White |
| 7,338,484 B2 | 3/2008 | Schoon et al. |
| 7,361,189 B2 | 4/2008 | Case et al. |
| 7,371,258 B2 | 5/2008 | Woo et al. |
| 7,374,571 B2 | 5/2008 | Pease et al. |
| 7,377,938 B2 | 5/2008 | Sarac et al. |
| 7,381,218 B2 | 6/2008 | Schreck |
| 7,381,219 B2 | 6/2008 | Salahieh et al. |
| 7,393,358 B2 | 7/2008 | Malewicz |
| 7,393,360 B2 | 7/2008 | Spenser et al. |
| 7,399,315 B2 | 7/2008 | Iobbi |
| 7,402,171 B2 | 7/2008 | Osborne et al. |
| 7,410,499 B2 | 8/2008 | Bicer |
| 7,416,530 B2 | 8/2008 | Turner et al. |
| 7,422,603 B2 | 9/2008 | Lane |
| 7,431,733 B2 | 10/2008 | Knight |
| 7,435,257 B2 | 10/2008 | Lashinski et al. |
| 7,445,632 B2 | 11/2008 | McGuckin, Jr. et al. |
| 7,455,689 B2 | 11/2008 | Johnson |
| 7,470,284 B2 | 12/2008 | Lambrecht et al. |
| 7,470,285 B2 | 12/2008 | Nugent et al. |
| 7,473,275 B2 | 1/2009 | Marquez |
| 7,481,838 B2 | 1/2009 | Carpentier et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,510,572 B2 | 3/2009 | Gabbay |
| 7,510,575 B2 | 3/2009 | Spenser et al. |
| 7,513,909 B2 | 4/2009 | Lane et al. |
| 7,534,261 B2 | 5/2009 | Friedman |
| 7,556,646 B2 | 7/2009 | Yang et al. |
| 7,578,828 B2 | 8/2009 | Gittings et al. |

(56) References Cited

U.S. PATENT DOCUMENTS

| | | | |
|---|---|---|---|
| 7,585,321 B2 | 9/2009 | Cribier | |
| 7,591,848 B2 | 9/2009 | Allen | |
| 7,618,446 B2 | 11/2009 | Andersen et al. | |
| 7,625,403 B2 | 12/2009 | Krivoruchko | |
| 7,632,296 B2 | 12/2009 | Malewicz | |
| 7,682,390 B2 | 3/2010 | Seguin | |
| 7,780,726 B2 | 8/2010 | Seguin | |
| 7,846,203 B2 | 12/2010 | Cribier | |
| 7,846,204 B2 | 12/2010 | Letac et al. | |
| 7,896,915 B2 | 3/2011 | Guyenot et al. | |
| 7,914,575 B2 | 3/2011 | Guyenot et al. | |
| 7,947,075 B2 | 5/2011 | Goetz et al. | |
| 7,959,672 B2 | 6/2011 | Salahieh et al. | |
| 8,002,825 B2 | 8/2011 | Letac et al. | |
| 8,052,749 B2 | 11/2011 | Salahieh et al. | |
| 8,057,540 B2 | 11/2011 | Letac et al. | |
| 8,092,518 B2 | 1/2012 | Schreck | |
| 8,092,520 B2 * | 1/2012 | Quadri | A61F 2/82 623/1.36 |
| 8,403,983 B2 | 3/2013 | Quadri | |
| 8,603,159 B2 | 12/2013 | Seguin et al. | |
| 8,628,571 B1 | 1/2014 | Hacohen et al. | |
| 8,926,690 B2 * | 1/2015 | Kovalsky | A61F 2/2418 623/1.26 |
| 8,992,604 B2 * | 3/2015 | Gross | A61F 2/2412 623/2.11 |
| 9,351,831 B2 | 5/2016 | Braido et al. | |
| 10,245,143 B2 * | 4/2019 | Gross | A61F 2/2439 |
| 2001/0007956 A1 | 7/2001 | Letac et al. | |
| 2001/0039450 A1 | 11/2001 | Pavcnik et al. | |
| 2002/0177894 A1 | 11/2002 | Acosta et al. | |
| 2003/0023300 A1 | 1/2003 | Bailey et al. | |
| 2003/0028213 A1 | 2/2003 | Thill et al. | |
| 2003/0040792 A1 | 2/2003 | Gabbay | |
| 2003/0042186 A1 | 3/2003 | Boyle | |
| 2003/0109924 A1 | 6/2003 | Cribier | |
| 2003/0114913 A1 | 6/2003 | Spenser et al. | |
| 2004/0019374 A1 | 1/2004 | Hojeibane et al. | |
| 2004/0044361 A1 | 3/2004 | Frazier et al. | |
| 2004/0044400 A1 | 3/2004 | Cheng et al. | |
| 2004/0093060 A1 | 5/2004 | Seguin et al. | |
| 2004/0093063 A1 | 5/2004 | Wright et al. | |
| 2004/0106976 A1 | 6/2004 | Bailey et al. | |
| 2004/0186563 A1 | 9/2004 | Lobbi | |
| 2004/0210304 A1 | 10/2004 | Seguin et al. | |
| 2004/0254594 A1 | 12/2004 | Alfaro | |
| 2004/0260389 A1 | 12/2004 | Case et al. | |
| 2005/0043759 A1 | 2/2005 | Chanduszko | |
| 2005/0043790 A1 | 2/2005 | Seguin | |
| 2005/0070794 A1 | 3/2005 | Deal et al. | |
| 2005/0070957 A1 | 3/2005 | Das | |
| 2005/0113910 A1 | 5/2005 | Paniagua et al. | |
| 2005/0137681 A1 | 6/2005 | Shoemaker et al. | |
| 2005/0137688 A1 * | 6/2005 | Salahieh | A61F 2/2412 623/2.11 |
| 2005/0137696 A1 | 6/2005 | Salahieh et al. | |
| 2005/0137702 A1 | 6/2005 | Haug et al. | |
| 2005/0182483 A1 | 8/2005 | Osborne et al. | |
| 2005/0267523 A1 | 12/2005 | Devellian et al. | |
| 2005/0283231 A1 | 12/2005 | Haug et al. | |
| 2005/0288706 A1 | 12/2005 | Widomski et al. | |
| 2006/0004442 A1 * | 1/2006 | Spenser | A61F 2/2472 623/1.21 |
| 2006/0058872 A1 | 3/2006 | Salahieh et al. | |
| 2006/0122692 A1 | 6/2006 | Gilad et al. | |
| 2006/0161248 A1 | 7/2006 | Case et al. | |
| 2006/0259136 A1 | 11/2006 | Nguyen et al. | |
| 2006/0259137 A1 | 11/2006 | Artof et al. | |
| 2006/0265056 A1 | 11/2006 | Nguyen et al. | |
| 2006/0287717 A1 | 12/2006 | Rowe et al. | |
| 2007/0060998 A1 | 3/2007 | Butterwick et al. | |
| 2007/0061002 A1 | 3/2007 | Paul et al. | |
| 2007/0073387 A1 | 3/2007 | Forster et al. | |
| 2007/0118210 A1 | 5/2007 | Pinchuk | |
| 2007/0179600 A1 | 8/2007 | Vardi | |
| 2007/0198097 A1 | 8/2007 | Zegdi | |
| 2007/0213813 A1 | 9/2007 | Von Segesser et al. | |
| 2007/0239265 A1 | 10/2007 | Birdsall | |
| 2007/0239269 A1 | 10/2007 | Dolan et al. | |
| 2007/0244546 A1 | 10/2007 | Francis | |
| 2007/0282436 A1 | 12/2007 | Pinchuk | |
| 2008/0071361 A1 | 3/2008 | Tuval et al. | |
| 2008/0071362 A1 | 3/2008 | Tuval et al. | |
| 2008/0071366 A1 | 3/2008 | Tuval et al. | |
| 2008/0071368 A1 | 3/2008 | Tuval et al. | |
| 2008/0077234 A1 | 3/2008 | Styrc | |
| 2008/0125859 A1 | 5/2008 | Salahieh et al. | |
| 2008/0140189 A1 | 6/2008 | Nguyen et al. | |
| 2008/0161909 A1 | 7/2008 | Kheradvar et al. | |
| 2008/0177381 A1 | 7/2008 | Navia et al. | |
| 2008/0195199 A1 | 8/2008 | Kheradvar et al. | |
| 2008/0208327 A1 | 8/2008 | Rowe | |
| 2008/0228263 A1 | 9/2008 | Ryan | |
| 2008/0234814 A1 | 9/2008 | Salahieh et al. | |
| 2008/0255660 A1 | 10/2008 | Guyenot et al. | |
| 2008/0269878 A1 | 10/2008 | Iobbi | |
| 2008/0275550 A1 | 11/2008 | Kheradvar et al. | |
| 2009/0005863 A1 | 1/2009 | Goetz et al. | |
| 2009/0164006 A1 | 6/2009 | Seguin et al. | |
| 2009/0171432 A1 | 7/2009 | Von Segesser et al. | |
| 2009/0171447 A1 | 7/2009 | Von Segesser et al. | |
| 2009/0276040 A1 | 11/2009 | Rowe et al. | |
| 2009/0287299 A1 | 11/2009 | Tabor et al. | |
| 2010/0082094 A1 * | 4/2010 | Quadri | A61F 2/2418 29/890.132 |
| 2010/0168839 A1 | 7/2010 | Braido et al. | |
| 2011/0040374 A1 | 2/2011 | Goetz et al. | |
| 2011/0098802 A1 | 4/2011 | Braido et al. | |
| 2011/0137397 A1 | 6/2011 | Chau et al. | |
| 2011/0224780 A1 | 9/2011 | Tabor et al. | |
| 2011/0264196 A1 | 10/2011 | Savage et al. | |
| 2012/0101571 A1 | 4/2012 | Thambar et al. | |
| 2012/0101572 A1 | 4/2012 | Kovalsky et al. | |
| 2012/0116496 A1 | 5/2012 | Chuter et al. | |
| 2012/0123529 A1 | 5/2012 | Levi et al. | |
| 2012/0172982 A1 | 7/2012 | Stacchino et al. | |
| 2012/0179244 A1 * | 7/2012 | Schankereli | A61F 2/2418 623/2.11 |
| 2012/0303116 A1 | 11/2012 | Gorman et al. | |
| 2013/0190857 A1 * | 7/2013 | Mitra | A61L 31/06 623/1.36 |
| 2013/0190861 A1 | 7/2013 | Chau et al. | |
| 2013/0310928 A1 * | 11/2013 | Morriss | A61F 2/2466 623/2.18 |
| 2014/0142694 A1 * | 5/2014 | Tabor | A61F 2/07 623/2.18 |
| 2014/0194981 A1 | 7/2014 | Menk et al. | |
| 2014/0243966 A1 * | 8/2014 | Garde | A61F 2/2418 623/2.18 |
| 2014/0277419 A1 * | 9/2014 | Garde | A61F 2/2403 623/2.18 |
| 2014/0277423 A1 * | 9/2014 | Alkhatib | A61F 2/2436 623/2.38 |
| 2014/0350668 A1 | 11/2014 | Delaloye et al. | |
| 2017/0112621 A1 * | 4/2017 | Salahieh | A61F 2/2433 |
| 2018/0263765 A1 | 9/2018 | Flaction | |

FOREIGN PATENT DOCUMENTS

| | | |
|---|---|---|
| AU | 2009200985 A1 | 4/2009 |
| CA | 2634358 A1 | 6/2007 |
| CA | 2657839 A1 | 3/2008 |
| CA | 2659690 A1 | 3/2008 |
| DE | 20003874 U1 | 5/2000 |
| DE | 19857887 A1 | 7/2000 |
| DE | 102005003632 A1 | 8/2006 |
| DE | 202007005491 U1 | 6/2007 |
| EP | 0592410 A1 | 4/1994 |
| EP | 0657147 A2 | 6/1995 |
| EP | 0696447 A2 | 2/1996 |
| EP | 0943302 A2 | 9/1999 |
| EP | 1093771 A2 | 4/2001 |

(56) References Cited

FOREIGN PATENT DOCUMENTS

| | | | |
|---|---|---|---|
| EP | 12511797 A1 | 10/2002 | |
| EP | 1262201 A1 | 12/2002 | |
| EP | 1264582 A2 | 12/2002 | |
| EP | 1267753 A2 | 1/2003 | |
| EP | 1598031 A2 | 11/2005 | |
| EP | 1968491 A2 | 9/2008 | |
| EP | 2033593 A1 | 3/2009 | |
| EP | 2047824 A1 | 4/2009 | |
| EP | 2059192 A1 | 5/2009 | |
| EP | 2074964 A1 | 7/2009 | |
| EP | 3616652 B1 | 3/2013 | |
| EP | 3616652 A1 | 3/2020 | |
| FR | 2815844 A1 | 5/2002 | |
| FR | 2874812 A1 | 3/2006 | |
| FR | 2932376 A1 * | 12/2009 | ........... A61F 2/2412 |
| WO | 9117720 A1 | 11/1991 | |
| WO | 9829057 A1 | 7/1998 | |
| WO | 0028922 A1 | 5/2000 | |
| WO | 0047139 A1 | 8/2000 | |
| WO | 0053122 A1 | 9/2000 | |
| WO | 0149213 A2 | 7/2001 | |
| WO | 0156500 A2 | 8/2001 | |
| WO | 0156505 A1 | 8/2001 | |
| WO | 0162189 A1 | 8/2001 | |
| WO | 0176510 A2 | 10/2001 | |
| WO | 02067782 A2 | 9/2002 | |
| WO | 02076349 A1 | 10/2002 | |
| WO | 03003949 A1 | 1/2003 | |
| WO | 03047468 A1 | 6/2003 | |
| WO | 03063729 A2 | 8/2003 | |
| WO | 2005070343 A1 | 8/2005 | |
| WO | 2005102015 A2 | 11/2005 | |
| WO | 2006058163 A2 | 6/2006 | |
| WO | 2006068944 A2 | 6/2006 | |
| WO | 2006076890 A1 | 7/2006 | |
| WO | 2006083763 A1 | 8/2006 | |
| WO | 2006086135 A2 | 8/2006 | |
| WO | 2006086736 A2 | 8/2006 | |
| WO | 2006127765 A1 | 11/2006 | |
| WO | 2007009117 A1 | 1/2007 | |
| WO | 2007071436 A2 | 6/2007 | |
| WO | 2007071436 A3 | 6/2007 | |
| WO | 2008028569 A1 | 3/2008 | |
| WO | 2008040555 A2 | 4/2008 | |
| WO | 2008070442 A1 | 6/2008 | |
| WO | 2009024859 A2 | 2/2009 | |
| WO | 2009053497 A1 | 4/2009 | |
| WO | 2009091509 A1 | 7/2009 | |
| WO | 2010008548 A2 | 1/2010 | |
| WO | 2010045238 A2 | 4/2010 | |
| WO | 2010045297 A2 | 4/2010 | |
| WO | 2010049160 A1 | 5/2010 | |
| WO | 2010083558 A1 | 7/2010 | |
| WO | 2011051043 A1 | 5/2011 | |
| WO | 2011057087 A1 | 5/2011 | |
| WO | 2011133787 A1 | 10/2011 | |
| WO | 2012048035 A2 | 4/2012 | |
| WO | 2012177942 A2 | 12/2012 | |
| WO | 2013033791 A1 | 3/2013 | |
| WO | 2013086132 A1 | 6/2013 | |
| WO | 2013134214 A1 | 9/2013 | |
| WO | 2014072439 A1 | 5/2014 | |
| WO | 2014121042 A1 | 8/2014 | |
| WO | 2014139545 A1 | 9/2014 | |
| WO | 2014158710 A2 | 10/2014 | |
| WO | 2014163706 A1 | 10/2014 | |

* cited by examiner

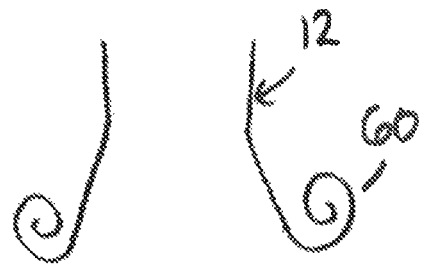
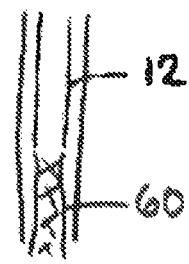
FIG. 7A  FIG. 7B
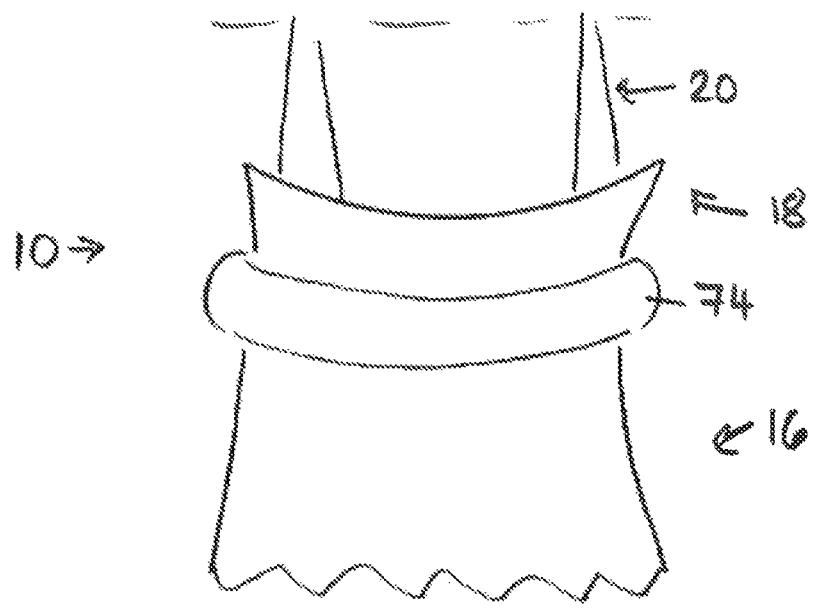
FIG. 8

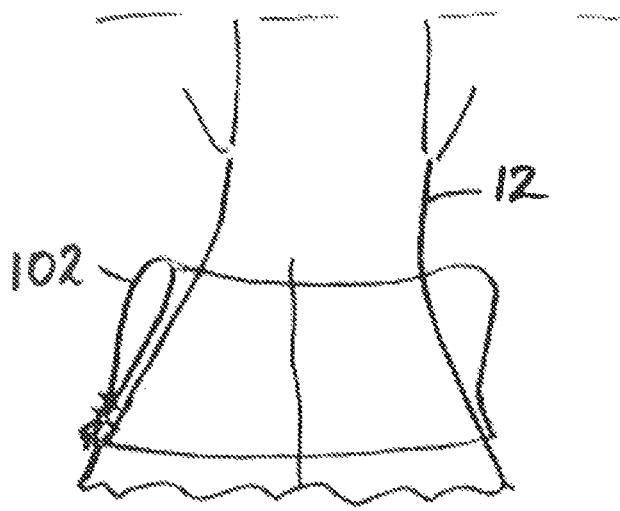
FIG. 12
FIG. 13
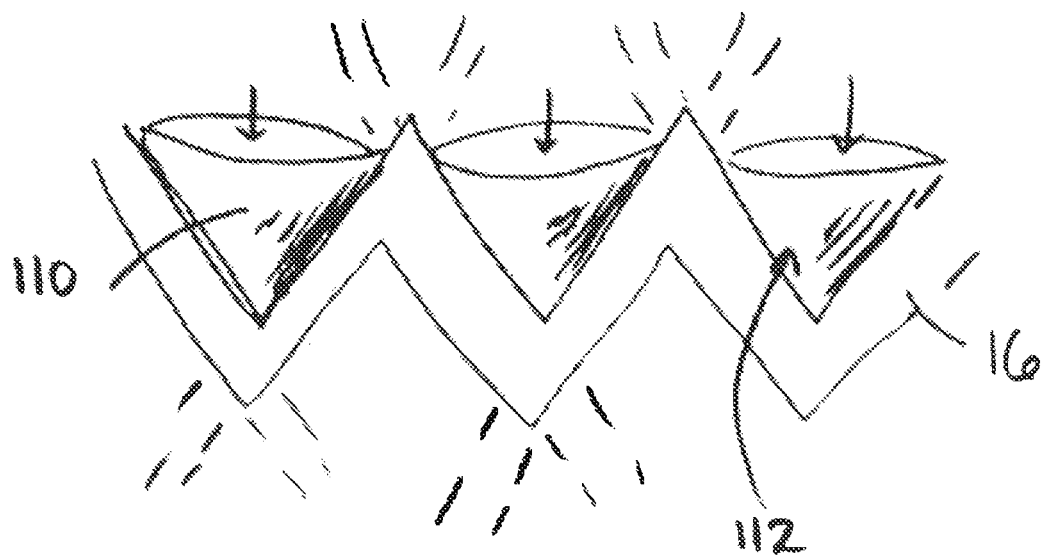

RELATING TO TRANSCATHETER STENT-VALVES

CROSS-REFERENCE TO RELATED APPLICATIONS

This application claims the benefit of priority of U.S. application Ser. No. 15/344,135 filed Nov. 4, 2016, which is a continuation of U.S. application Ser. No. 14/879,482 filed Oct. 9, 2015, which is a continuation of U.S. application Ser. No. 13/839,357 filed Mar. 15, 2013, the entirety of these applications of which are hereby incorporated by reference.

RELATED APPLICATIONS

The present disclosure claims priority to European patent application no. EP 12 002 015.1 filed, Mar. 22, 2012, the entire disclosure of which is herein incorporated by reference.

FIELD OF THE DISCLOSURE

The present disclosure relates to the field of transcatheter stem-valves. In some embodiments, the stent-valve may be a cardiac valve, for example, an aortic valve.

BACKGROUND

Transcatheter valve implantation (for example, transcatheter aortic valve implantation (TAVI)) is an evolving technology for replacement valve therapy that (i) avoids the trauma of conventional open-chest surgery, and (ii) avoids the need for heart and lung bypass. In such a technique, a stent-valve is compressed and loaded into a delivery catheter. The delivery catheter is introduced to the desired site of implantation (for example at the heart) via a percutaneous route or via minimally invasive surgery. The stent-valve is deployed into the implantation position from or by the delivery catheter, and the delivery catheter is then withdrawn.

Despite the successes of transcatheter stent-valves, technological challenges remain. One such challenge is preventing leakage of blood around the stent-valve (so called para-valve leakage). The above stents form a friction fit with the native anatomy to anchor the stent-valve in position, and are round in cross-section. However, the native anatomy in which the stent is implanted is often off-round and is different for each person. Moreover, heavy calcification of the native anatomy may obstruct full deployment of any stent, and make the native anatomy even more irregular. It can sometimes be difficult to provide a perfectly sealing fit between the stent-valve and the surrounding anatomy.

In order to address para-valve leakage, it is known to incorporate an external skirt or cover as part of the stent-valve. For example, the skirt is made of compressible biocompatible material, such as pericardial tissue or PET. The thicker the material of the skirt, the more able the skirt is to occlude gaps and effect a seal. However, a disadvantage is that such skirts add to the bulk of the stent-valve. A thick skirt makes the stent-valve problematic to compress to a desirably small size for implantation.

It would be desirable to provide a technique for mitigating para-valve leakage without substantially hindering the compressibility of a stent-valve.

SUMMARY OF THE DISCLOSURE

In some embodiments of the present disclosure, a stent-valve for transcatheter delivery is provided, with the stent-valve comprising a stent supporting a plurality of valve leaflets.

In some embodiments, a seal for mitigating para-valve leakage (which may be referred herein throughout either as "seal" or "para-valve leakage seal") is provided. The seal may be of flexible and/or compliant material.

In some embodiments, the seal is carried by at least one seal support. The seal support may be collapsible to a stowed condition in which the seal is relatively streamlined or compressed with respect to the stent when the stent is compressed. For example, in the stowed condition, the seal support may be generally coplanar with the body of the stent, or may be arranged compressed against the stent. The seal support may be deployable to a deployed condition in which the support holds or biases the seal to a deployed state with respect to the stent. The seal support may be self-deploying from the stowed condition to the deployed condition. For example, the seal support may be constrainable in the stowed condition by sheathing of the stent in a compressed state for delivery. The seal support may be self-deploying from the stored state when the effect of the constraining sheath is removed. The seal support may be of shape memory material, for example, nitinol.

Various forms and structure of seal support are envisaged. In some embodiments, the seal support may be integral with the stent (e.g. integrally formed as part of the stent). In other forms, the seal support may be distinct from the stent. Such a seal support may optionally be coupled to or captive on the stent.

The seal support may be configured to bear against the material of the seal without penetrating through the seal material. For example, the seal support may have a shape that distributes contact force. A function of the seal support may be to urge the seal outwardly without the seal support penetrating through the seal material or into a tissue surface against which the seal is desired.

In some embodiments, the seal support may comprise a biasing element that biases the seal to a deployed condition (for example). The seal support (e.g. biasing element) may comprise, for example, a cantilever element (or a plurality of cantilever elements). The cantilever elements may be capable of flexing independently of one another, in order to provide a high degree of local seal conformity against an irregular lumen or tissue surface. In some embodiments, each cantilever element is associated with a respective aperture of a lattice structure of the stent. The cantilever elements may, for example, have one end coupled (or integral) with the stent body, and an opposite or remote end that is free to deploy outwardly. The remote end may have a rounded or enlarged or pad tip to avoid having a sharp end that might otherwise risk penetrating through the seal material. The cantilever elements may extend generally in the same direction as each other (e.g. having the remote end directed to one end (such as the outflow end) of the stent-valve), or the cantilever elements may be arranged in two opposite directions (e.g. at least one pointing towards the outflow end, and at least another pointing towards the inflow end), or the cantilever elements may be arranged in a variety of different directions. In some embodiments, the seal support comprises a ring shape, or tubular shape, or annular member. The member may have an annular coil shape.

In some embodiments, the seal support comprises a member that can be stowed in a generally elongate or helical form, and which deploys to a radially expanded loop form.

In some embodiments, the seal support comprises a portion of the stent that everts from a stowed condition to a deployed condition. Eversion of the stent can provide radial expansion upon deployment without increasing significantly the diameter of the stent when compressed (de-everted). For example, an inflow end or portion of the stent may evert towards the outflow end.

In some embodiments, the stent carries a sealing skirt (or web). The seal support may bias the skirt (or portions thereof) radially outwardly to distend away from the body of the stent.

Additionally or alternatively to embodiments noted above for a seal support, a seal of the stent-valve may be configured to be responsive to direction of blood flow past the seal, relative to inflow and outflow ends of the stent-valve. The seal may be configured such that blood flow in a reverse direction (for outflow to inflow) biases the seal to a deployed state to obstruct such flow.

For example, in some embodiments, the seal may comprise at least one web defining one or more pockets. The one or more pockets may be configured to fill with blood (or blood components) in response to blood flow in the reverse direction, such that the pocket distends outwardly. Distention of the pocket can fill a gap between the stent-valve and the surrounding anatomy, to obstruct the reverse flow of blood past the pocket.

In some embodiments, the pocket may be defined or carried at a respective aperture of a lattice structure of the stent. The pocket may be defined at least partly by an outer skirt carried on an exterior of the stent. Additionally or alternatively, the pocket may be defined at least partly by an inner skirt carried on an interior of the stent.

Additionally or alternatively to the above embodiments, a seal may comprise a skirt at least a portion of which is captive with respect to the stent, and at least a further portion of which is free to deploy or float relative to the stent.

In some embodiments, the further portion may contact a surrounding tissue or lumen wall before the body of the stent is fully deployed. As part of the deployment procedure, the stent may be displaced or biased in a first axial direction to seat against native leaflets. The frictional contact of the skirt against the tissue may cause the further portion of the skirt to bunch or wrinkle in the axial direction during the displacement action. Such bunching or wrinkling may provide additional material to fill voids or gaps between the stent and the surrounding tissue.

Additionally or alternatively, in some embodiments, the further portion of the skirt may seal may be responsive to direction or paravalve blood flow or to pressure blood. The further portion may, for example, deploy outwardly to contact a surrounding tissue lumen wall. The further portion may form a generally channel shape in response to pressure of blood or flow of blood in the reverse direction. The channel shape may bias an outer portion of the skirt to seat against the surrounding tissue or lumen surface.

Additionally or alternatively to the above embodiments, a seal of the stent-valve may be embossed to present a non-smooth surface. For example, the embossing may be defined by one or more sutures. The one or more sutures may define a zig-zag pattern. The suture may define a generally continuous embossment to obstruct blood flow past the stent.

Additionally or alternatively to the above embodiments, a seal of the stent-valve may be generally oversized compared to the diameter of the stent. The seal may be bunched or pleated by connections (e.g. suturing) to the stent that causes bunching or pleating between the connections. The bunching/pleating may create additional compliant bulk of seal material able to fill voids or gaps between the stent-valve and the surrounding tissue or lumen surface. The positions of the connections may define bunching or pleating in directions in a pattern that obstructs leakage of blood.

Additionally or alternatively to the above embodiments, a seal of the stent-valve may be configured to be self-expanding or self-filling due to a physical property of the seal.

For example, in some embodiments, the seal may be of or comprise a foam, sponge or fibrous material. Such a material may self-expand resiliently when the stent deploys. Additionally or alternatively, such a material may absorb blood (and/or components thereof) within its pores or interstices in order to expand the material physically or add bulk.

In some embodiments, the seal may be generally flat and/or tubular in a stowed state, and may roll or curl into an annular bead or doughnut when in a deployed state. The seal may be self-biased to the deployed state, but be resiliently deformable to the stowed state during compression of the stent for loading into a delivery apparatus. Upon removal of a constraining effect of a sheath of the delivery apparatus, the seal may be configured to readopt the deployed state, in order to provide a radially enlarged seal around the stent.

in some embodiments, at least a portion of the stent comprises a lattice structure, and the stent-valve further comprises one or more seals deployable from or through apertures of the lattice. In one form, the seals comprise web portions of material that define pockets associated with respective apertures of the lattice. The web portions may be configured to distend outwardly from the respective apertures. For example, in some embodiments, the web portions define pockets open on or to one side such that a respective pocket fills with blood to distend outwardly from the aperture of the lattice. Additionally or alternatively, the lattice structure of the stent may comprise biasing elements for biasing the web portions (e.g. pockets) of material radially outwardly from the lattice structure.

In some embodiments, the stent carries a sealing skirt (or web). The stent may comprise biasing elements for biasing the skirt (or portions thereof) radially outwardly to distend away from the body of the stent. The sealing skirt may optionally be carried on the exterior of the stent. An inner skirt (or web) may optionally be carried on the interior of the stem (and optionally coupled directly to the leaflets). At least one of the skirts may be of fabric (e.g. PET). Additionally or alternatively, at least one of the skirts may be of biological tissue, for example, pericardium.

In some embodiments, a biasing element distinct from the stent may bias a seal outwardly. For example, the biasing element may be a ring element (e.g. closed ring or split ring), within an annular seal. The biasing element may be compressible with the stent to a radially compressed condition. The biasing element may expand (e.g. self-expand) towards a radially expanded state when the stent is deployed. The biasing element may be of shape memory material, e.g. nitinol.

Certain features, ideas and advantages of the embodiments taught by the present disclosure are identified above and/or in the appended claims, but these do not limit any embodiment or invention disclosed herein. Protection is claimed for any novel idea or feature described herein and/or illustrated in the drawings whether to not emphasis has been placed thereon.

BRIEF DESCRIPTION OF THE DRAWINGS

Non-limiting embodiments of the disclosure are illustrated in the accompanying drawings, in which:

FIG. 7a is a schematic side view of a seal arrangement comprising a rollable cuff when in a deployed state, and FIG. 7b is a schematic view of the seal arrangement when in a stowed, sheathed state, each according to some embodiments of the disclosure.

FIG. 8 is a schematic side view of a seal arrangement comprising a porous material, according to some embodiments of the disclosure.

FIG. 12 is a schematic illustration of an alternative seal arrangement using a folded skirt, according to some embodiments of the disclosure.

FIG. 13 is a schematic illustration of an alternative seal arrangement using distensible pockets, according to some embodiments of the disclosure.

DETAILED DESCRIPTION

Figure 1:
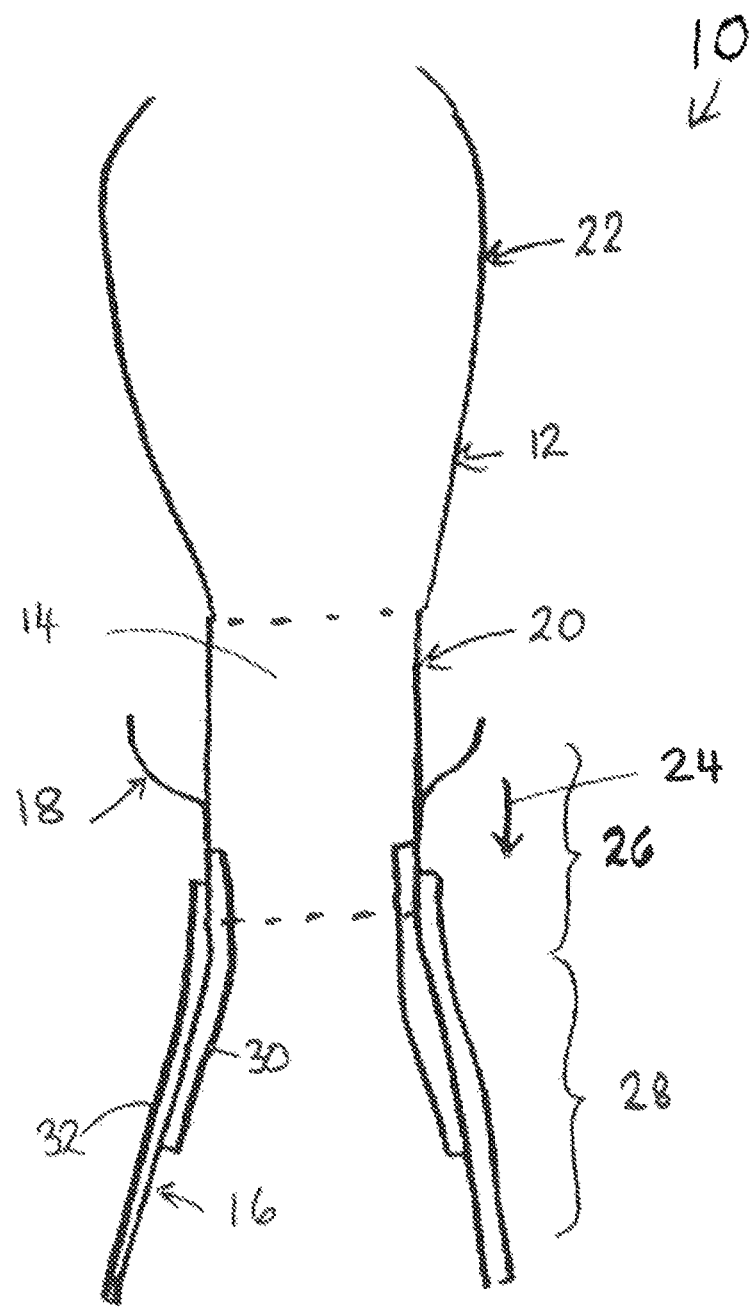
FIG. 1 is a schematic drawing illustrating a stent-valve 10, according to some embodiments of the disclosure.

Referring to FIG. 1 (and FIG. 18), a cardiac stent-valve 10 is illustrated for transcatheter implantation. The stent-valve 10 may be cardiac stent-valve, for example, an aortic stent-valve, a mitral stent-valve, a pulmonary stent-valve or a tricuspid stent-valve, for implantation at the respective valve position in a human heart.

The stent-valve 10 may optionally comprise biological tissue (for example, pericardium (such as porcine pericardium and/or bovine pericardium) and/or natural cardiac valve leaflets (for example, natural porcine cardiac valve leaflets, optionally attached to a portion of natural cardiac wall tissue). The biological tissue may be fixed, for example, using glutaraldehyde.

The stent-valve 10 may be compressible to a radially compressed condition (not shown) for delivery using a delivery catheter, and be expandable to an expanded condition (as shown) at implantation. The stent-valve 10 may comprise a stem 12 carrying a plurality of leaflets defining a valve 14. Various geometries of stent 12 may be used in some embodiments, the stent 12 may include one of more of: a lower tubular or crown portion 16; an upper crown portion 18; a plurality of upstanding commissural supports 20; and a plurality of stabilization arches 22. In use, the lower portion 16 of the stent 12 may be configured to be deployed after the other regions of the stent 12 have first been at least partly deployed. For example, the arches 22, the supports 20 and the upper crown 18 may be deployed at least partly before the lower portion 16 (in that order, or in reverse order, or in a different order). At least once the upper crown 18 has been at least partly deployed, the stent 12 may be urged and/or displaced in the direction of arrow 24 to seat the upper crown 18 against native leaflets at the implantation site. Deploying the lower portion 16 last fixes the stent 12 in its final position.

At least the lower portion 16, and optionally a portion of the upper crown 18, may be formed by a lattice structure of the stent. The lattice structure may define apertures, for example, generally diamond-shaped apertures.

The native leaflets may generally overlap a portion 26 of the stent. The native valve annulus may overlap a portion 28 of the stent.

Optionally, the stem-valve 10 may further comprise an inner skirt 30 communicating with the leaflets 14 and carried on an interior of the stent 12. Additionally or alternatively, the stent-valve 10 may further comprise an outer skirt 32 carried on an exterior of the stent 12. When both skirts are provided, the skirts may partially overlap. The skirts may be offset such that one skirt (e.g. the outer skirt 32) extends further towards a lower extremity of the stent 12 than the other (e.g. inner skirt 30). Additionally or alternatively, one skirt (e.g. the inner skirt 30) extends further towards an upper extremity of the stent 12 than the other (e.g. outer skirt 32). The skirts may be of any suitable flexible and/or compliant material, for example, fabric (e.g. of PET), or of plastics film (e.g. of PET), or of biological tissue (e.g. of pericardium).

Optionally, at least the outer skirt 32 is positioned to leave the upper crown 18 substantially un-obscured by the outer skirt 32. Such an arrangement may assist good blood flow to the coronary arteries (for example, in the case of a stent-valve for the aortic valve).

In some embodiments, the lower portion 16 has an extremity formed with a substantially zig-zag shape. The zig-zag shape may comprise lower apexes 16a and upper apexes 16b. The upper apexes 16b may be masked in FIG. 1 by the superimposed presentation of both the front most and rearmost cells of the lattice structure. The zig-zag shape may be substantially continuous around the circumference of the stent 12. The outer skirt 32 may have a peripheral edge having a zig-zag shape that matches substantially the zig-zag shape of the extremity of the lower portion 16. Such an arrangement can avoid excessive material at the extremity, and thereby facilitate crimping of the stent-valve 10. At the same time, the outer skirt 32 covers (for example, complete) open cells of the lattice structure down to the stent extremity to reduce risk of blood leakage through the apertures of the cells. The outer skirt 32 can also provide a layer of material over the struts of the stent, thereby to cushion the engagement between the stent and the sensitive native heart tissue.

The valve 14 may comprise biological tissue, for example, pericardium (such as porcine pericardium or bovine pericardium) or natural cardiac valve leaflets (for example, natural porcine cardiac valve leaflets, optionally attached to a portion of natural cardiac wall tissue). Other biological or non-biological material could also be used for the valve 14, as desired.

The stent 12 may optionally be of a self-expanding type that is compressible to the compressed state for loading into a delivery catheter having a sheath for constraining the stent 12 in the compressed state for delivery to the site of implantation. In use, by removal of the constraining effect of the sheath, the stent 12 self-expands to or towards the expanded state. A self-expanding stent may, for example, me of shape-memory material, for example, shape-memory metal alloy, for example, nitinol. Alternatively, the stent 12 may be configured to be expanded by application of an expanding force from the delivery catheter, such as by using an expansion balloon.

There now follows a description of various seal configurations that may be used with the above-described stent-valve 10. The seal configurations may also be used with different stent shapes and configurations.

Figure 2A:
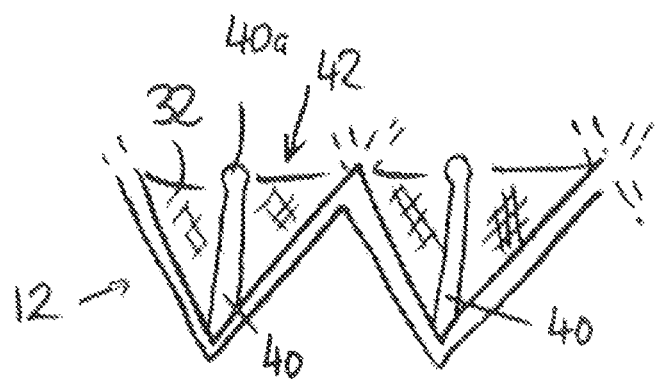
FIG. 2a is a front view of a seal arrangement with cantilevered seal supports.
Figure 2B:
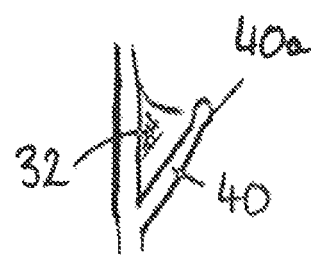
FIG. 2b is a side view of FIG. 2a in a deployed configuration, each according to some embodiments of the disclosure.

FIG. 2 illustrates a first example of seal support in the form of a plurality cantilever elements 40 mounted on or integral with the stent 12. Each cantilever element 40 may be associated with a respective aperture 42 of the lattice structure. Each cantilever element 40 may be bendable generally independently of the others. Each cantilever element 40 may be movable between a stowed condition, in which the cantilever element is generally co-planar with the portion of the stent 12 around the aperture 42 (or at least is compressed to lie directly or indirectly there against), and a deployed condition in which the cantilever element 40 is biased radially outwardly from the body (e.g. lower portion 16) of the stent 12 (FIG. 2b). The seal support urges a seal (e.g. the outer skirt 32) outwardly so as to fill gaps or voids between the stent-valve 10 and the surrounding lumen/tissue. The ability of the cantilever elements 40 to flex independently can provide a high degree of local conformity. Each cantilever element 40 may have a remote end 40a in the form of a rounded, or pad-like, or other non-damaging shape that can bear against the seal material to bias the seal radially outwardly, without penetrating through, or puncturing, the seal material.

The cantilever elements 40 may be arranged generally in the same orientation (e.g. with the remote ends 40a directed towards one end, e.g. the outlet end, of the stent 12), or distributed to be orientated in two opposite directions, or be distributed to be orientated in a variety of different directions.

The seal urged by the cantilever elements 40 may be generally continuous, or it may be discontinuous in the form of webs or pockets. The pockets may be arranged such that back-pressure of blood, or para-valvular blood flow in the reverse direction from outlet to inlet end of the stent 12, fills the pockets to cause the pockets further to distend, thereby enhancing the seal effect to obstruct such para-valvular flow. Further detail of such pockets is also described with reference to FIG. 13, and any of such features may also be used with the present example.

Figure 3:
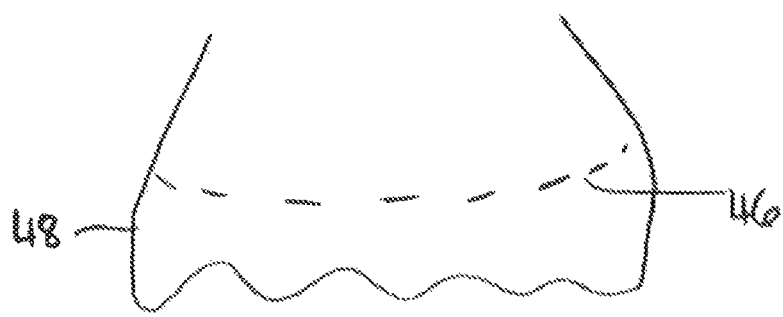
FIG. 3 is a schematic view of a seal arrangement with an annular wire seal support according to some embodiments of the disclosure.

Referring to FIG. 3, a seal support 46 is illustrated in the form of an annular wire or ring that is oversize compared to the stent 10. The annular wire is compressible to a stowed state when the stent is compressed, and expands to a deployed state when unconstrained, to urge the seal 48 to a radially expanded state to form a seal against the surrounding tissue/lumen.

Figure 4A:
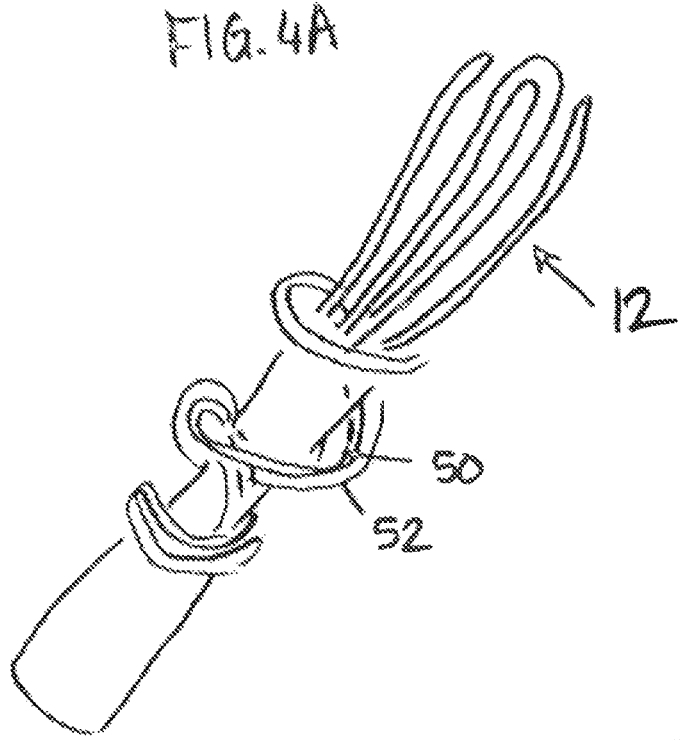
FIG. 4a is a schematic perspective view of an elongate seal support around the stent in a compressed state.
Figure 4B:
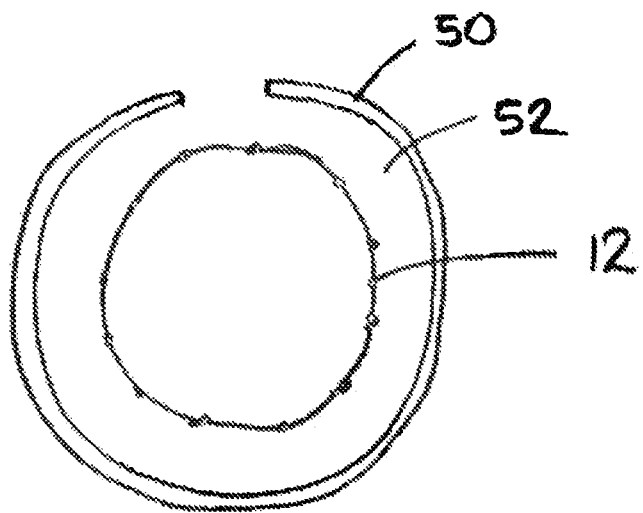
FIG. 4b is a schematic top view of the seal when in a deployed state, each according to some embodiments of the disclosure.

Referring to FIG. 4, a seal support 50 is illustrated in the form of an elongate member carrying a seal 52. The seal support is compressible to a stowed form (FIG. 4a) for example a helical shape around the stent 12 when in its compressed state. The seal support is expandable to a deployed state (FIG. 4b), for example, a radially expanded closed or semi-closed loop form in which the seal support presents the seal 52 in expanded form around the stent 12.

Figure 5A:
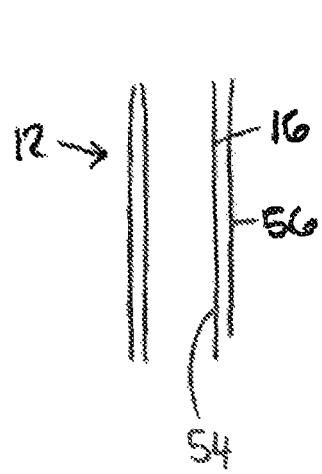
FIG. 5a is a schematic view of a seal arrangement in a sheathed non-everted state.
Figure 5B:
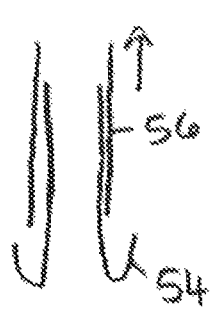
FIG. 5b shows initial unsheathing of the seal arrangement of FIG. 5a to permit everting.
Figure 5C:
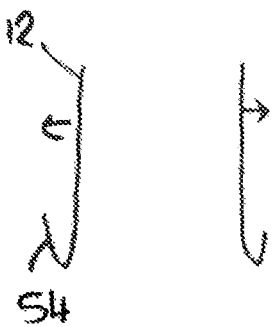
FIG. 5c shows the seal arrangement of FIG. 5a when unsheathed, each according to some embodiments of the disclosure.

Referring to FIG. 5, a seal support 54 is illustrated in the form of an everting portion of the lower region 16 of the stent 12. The seal support 54 is movable between a stowed, non-everted configuration and a deployed, everted configuration. In a compressed form constrained by a sheath 56 (FIG. 5a), the lower portion of the stent including the seal support 54 is generally tubular (non-evened). As the sheath 56 is progressively removed axially (FIG. 5b), the seal support 56 is unsheathed. Unconstrained, the seal support 56 everts to its deployed state in which the seal is presented and/or biased radially outwardly from the stent body. Further unsheathing of the stent 12 or the lower portion 16 (FIG. 5c) permits the stent 12 to expand to its expanded state. The everted seal support 54 urges the seal into tight sealing contact with the surrounding tissue/lumen. The seal may be carried on the inners surface of the stent when compressed, and presented in an outward direction when everted.

Figure 6:
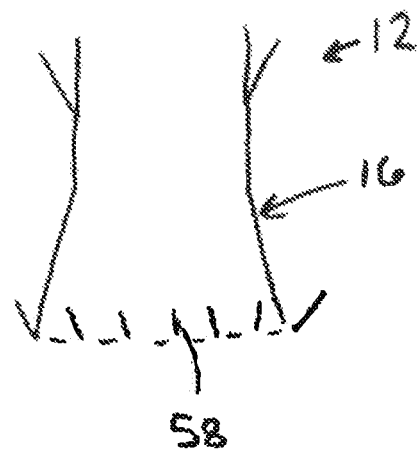
FIG. 6 is a schematic side view of a further example of seal arrangement with flexible cantilever arms, according to some embodiments of the disclosure.

FIG. 6 illustrates a seal support that is similar to both FIGS. 2 and 5. The seal support 58 comprises flexible cantilever elements at the lower portion 16 of the stent 12, similar to those of FIG. 2. The seal support 58 also resembles the everted state of the seal support 56 of FIG. 5. In the example of FIG. 6, the cantilever elements do not move between an everted and non-everted state. In the stowed state, the cantilever elements are generally flat against or within the structure of the stent 12 (similar to FIG. 2).

FIG. 7 illustrates a seal in the form of a rollable bead or cuff 60. The rollable cuff 60 may be self-biased or it may be supported by a seal support frame that tends to roll the cuff 60. In a stowed state (FIG. 7b), the cuff is unrolled to define a generally flat tubular form. The cuff may be constrained in the stowed state by a constraining sheath 62 of a delivery device. When unsheathed, the cuff 60 is free to move to its deployed state (FIG. 7a) in which the cuff 60 rolls up to define a cuff or bead shape. Such a seal provides a compliant bead of material to fill any gap between the stent 12 and the surrounding tissue/lumen.

FIG. 8 illustrates a seal 74 in the form of foam, or sponge or fibrous porous material. Such material is compressible when dry, because air is easily expelled from the pores and/or interstices of material when compressed. The seal 74 may therefore adopt a compressed state without increasing the bulk of the stent-valve 10 significantly. Once implanted, blood may penetrate and fill the pores and/or interstices of the seal material. The blood may become trapped in the pores and/or interstices, thereby creating a barrier to blood flow through the material. The blood may also cause distension of the seal material to further expand the seal outwardly and fill any gaps of voids around the stent-valve 10.

Figure 9A:
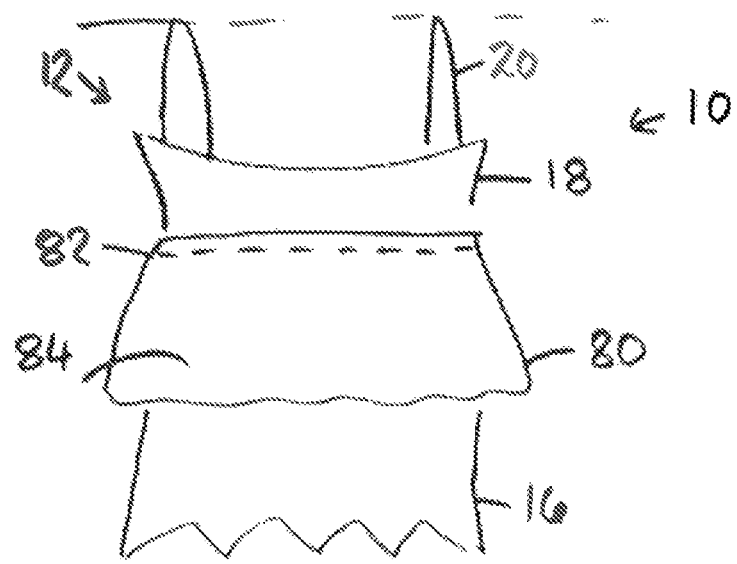
FIG. 9a is a schematic side view of a seal arrangement comprising a floating skirt.

FIG. 9 illustrates a seal in the form of a flexible skirt 80. The skirt 80 depends, for example, from the junction between the upper crown 18 and the lower portion 16 of the stent 16, to at least partly overlap the lower portion 16. A first (e.g. upper) portion 82 of the skirt 80 is coupled to the stent 12, to hold the skirt 80 captive. For example, the first portion 82 may be sutured to the stent 12. A second (e.g. depending) portion 84 of the skirt 80 is generally unconstrained, and is free to float relative to the stent 12.

Figure 9B:
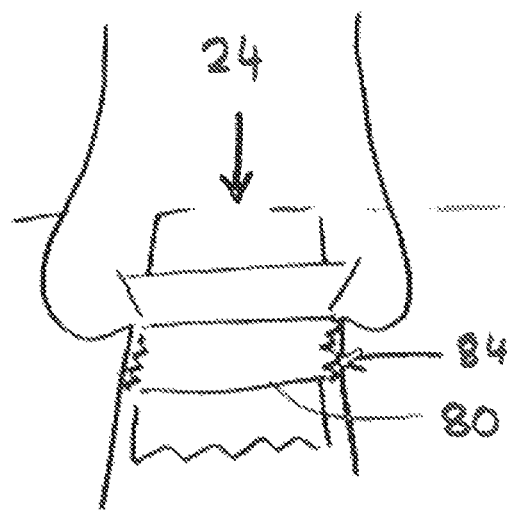
FIG. 9b is a schematic side view of the effect of the seal arrangement of FIG. 9a when implanted, according to some embodiments of the disclosure.

As illustrated in FIG. 9b (and explained above in relation to FIG. 1), the implantation procedure for the stent-valve 10 may involve displacing the stent-valve in the direction of arrow 24 to seat the upper crown 18 against native valve leaflets. The friction between the floating second portion 84 of the skirt 80, and the surrounding tissue/lumen may cause the second portion 84 to bunch or wrinkle axially, thus creating an excess of material that is able to seal any gap between the stent-valve 10 and the surrounding tissue/lumen.

Figure 10:
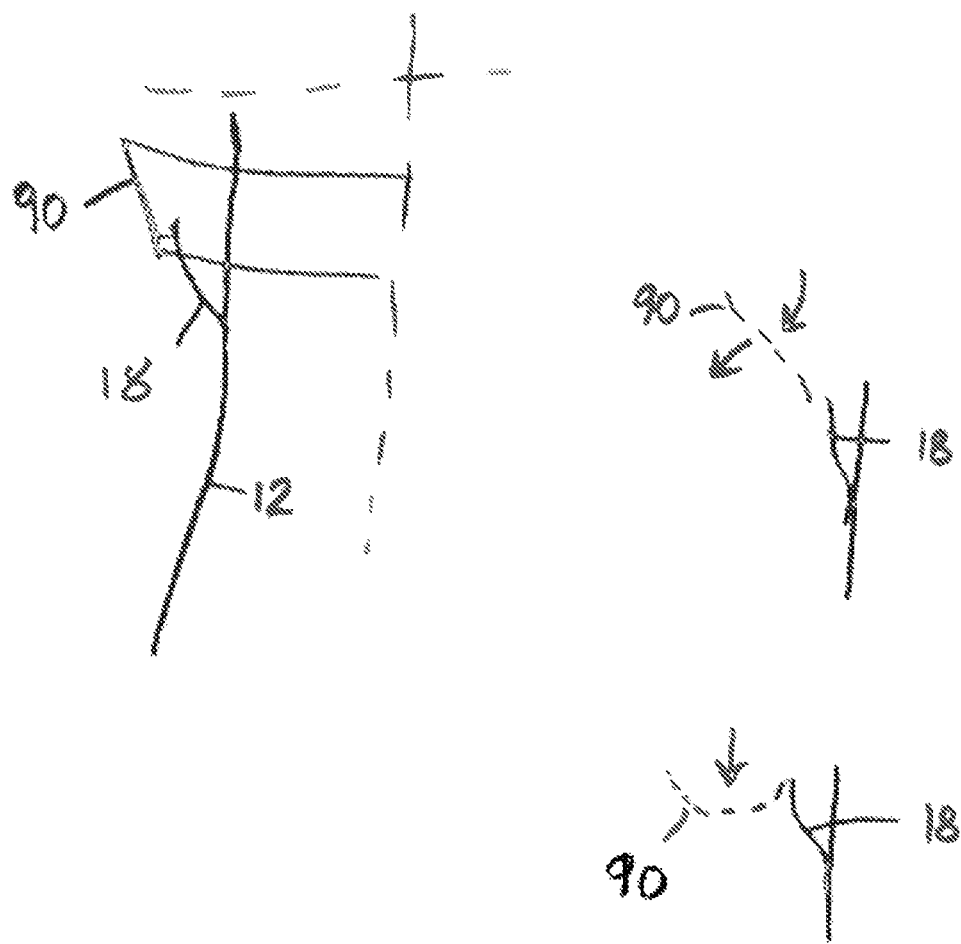
FIG. 10 is a schematic illustration of an alternative arrangement of a floating skirt seal, according to some embodiments of the disclosure.

FIG. 10 illustrates an alternative seal in the form of a flexible skirt 90. In contrast to the skirt of FIG. 9, the skirt 90 projects from the upper crown 18 towards the upper end of the stent 12. As indicated in phantom, under back pressure of blood, or reverse flow of blow around the stent-valve 10, the flexible skirt bears outwardly to seal against the surrounding tissue/lumen. The flexible skirt may form a channel shape section such that the back pressure of blood increases the sealing pressure against the surrounding tissue/lumen.

Figure 11:
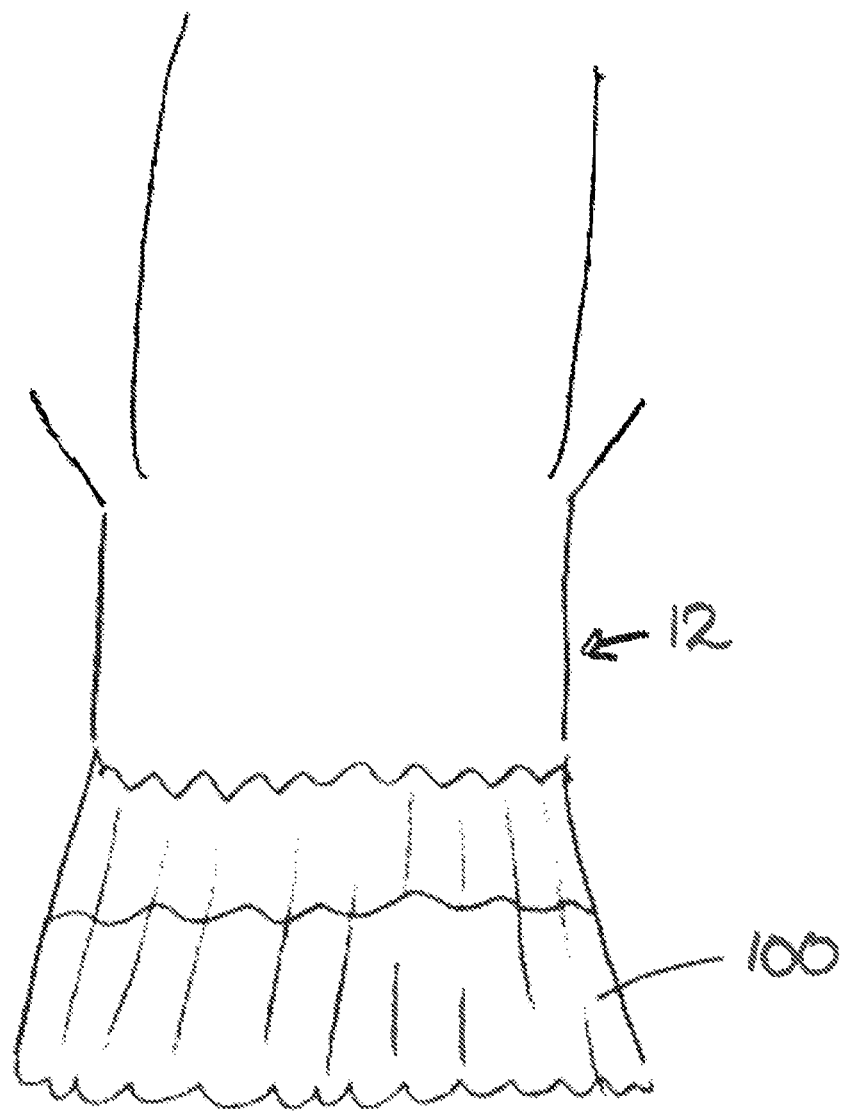
FIG. 11 is a schematic illustration of an alternative seal arrangement using a plated skirt, according to some embodiments of the disclosure.

FIG. 11 illustrates an alternative seal in the form of an oversized flexible skirt 100 that is connected to the stent 12 at one or more positions to define pleating or bunching. The connections may be by suturing. The pleating or bunching creates additional compliant material able to fill yids of gaps between the stent 12 and the surrounding tissue/lumen.

FIG. 12 illustrates an alternative seal in the form of a skirt that is folded to define a cuff 102. The skirt material is flexible, but the fold creates a radiused bend providing a natural bulge. The bulge biases the seal material outwardly in order to fill voids or gaps between the stent 12 and the surrounding tissue/lumen.

FIG. 13 illustrates an alternative seal comprising a plurality of flexible pockets 110. Each pocket may be associated with a respective aperture 112 of a lattice structure of the stent, for example, the lower portion 16 and/or the upper crown 18. The pocket 110 may be defined by a flexible web of material. One wall of the pocket may be define by a portion of the outer skirt. Another wall of the pocket may be defined by a portion of the inner skirt. The pocket may be open on one side facing towards the outlet end of the stent, and closed in the opposite direction. In a stowed state, the pocket may collapse or fold substantially flat so as not to increase the bulk of the stent-valve. Once deployed, the pocket may open either under the influence of natural resilience, or under the influence of blood back pressure entering the mouth of the pocket. The back pressure causes the pocket to distend outwardly against surrounding tissue/lumen, and thereby further obstructing leakage of blood around the outside of the stent-valve 10.

Figure 14:
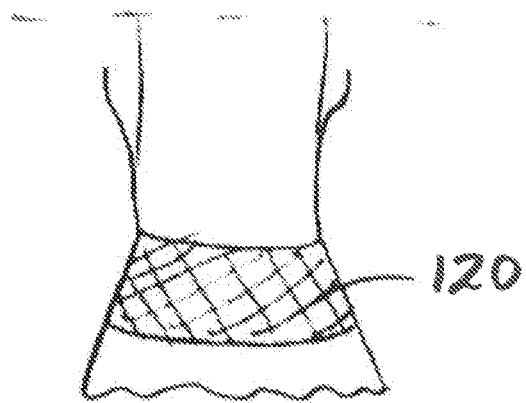
FIG. 14 is a schematic drawing of an alternative sealing arrangement using swellable material, according to some embodiments of the disclosure.

FIG. 14 illustrates an alternative seal arrangement comprising material 120 that swells in response to contact with blood. The swelling characteristics increase the bulk of the seal, enabling the seal to distend to fill any gaps between the stent-valve 10 and the surrounding tissue/lumen. Example swellable materials include a hydrogel and/or a liquid swellable polymer, and/or a so called superabsorbent material. The material may, for example, be carried by, or impregnated or otherwise embodied within the outer skirt. For example, the skirt may be of fabric comprising fibers of the swellable material. The material may be captive within a containing chamber, for example a flexible and/or distensible pouch or cuff. The combination of inner and outer skirts, with one comprising swellable material, can provide an especially effective seal arrangement. Further background information of use of, for example, a hydrogel for stent-valves may be found in US 2005/137688.

Figure 18:
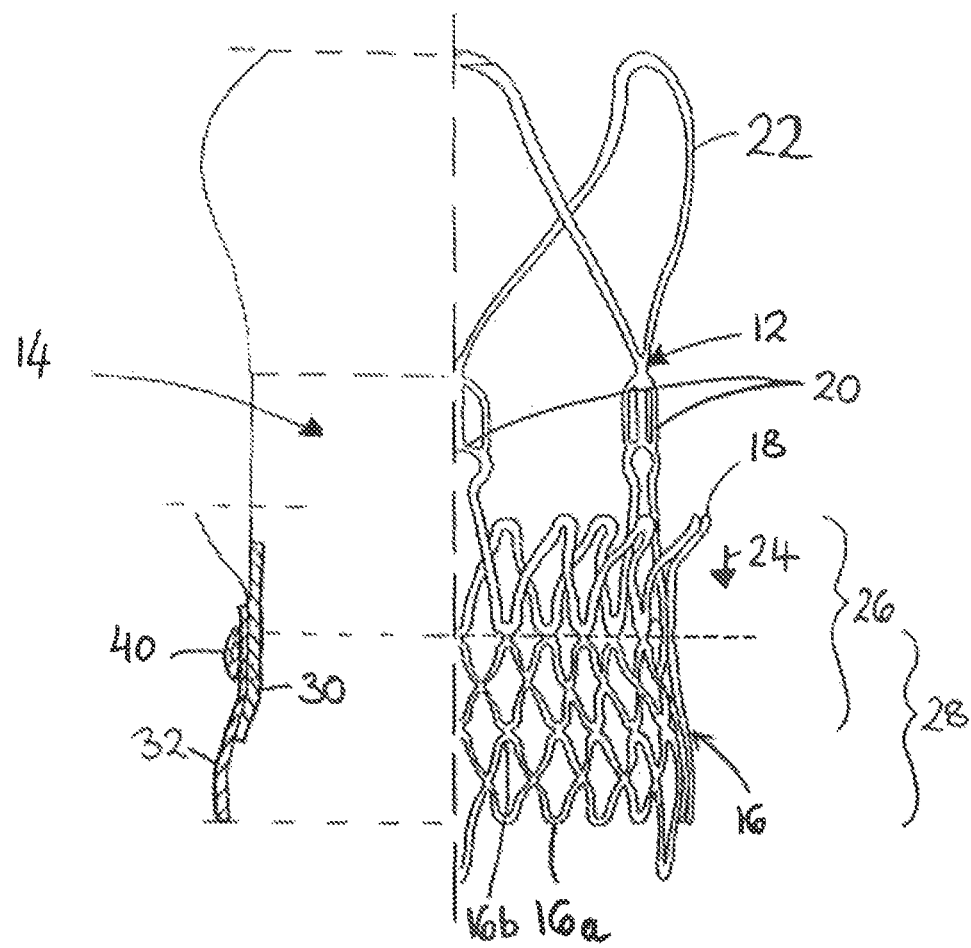
FIG. 18 is a partial schematic view of optional details of a stent-valve of FIG. 1, according to some embodiments of the disclosure.
Figure 19:
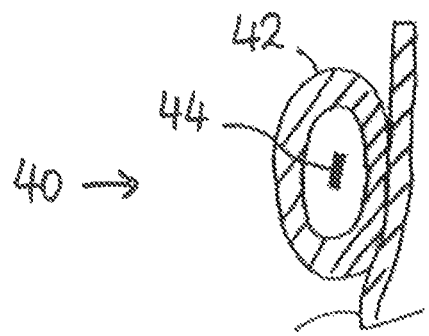
FIG. 19 is a schematic section of the paravalve seal of FIG. 18, according to some embodiments of the disclosure.

The seal of FIG. 14 is also illustrated in other embodiments of FIGS. 18 and 19. The swellable material is denoted by numeral 44, the containing chamber 42, together defining the paravalve seal 40 carried by, or comprised within, the outer skirt 32.

Figure 15:
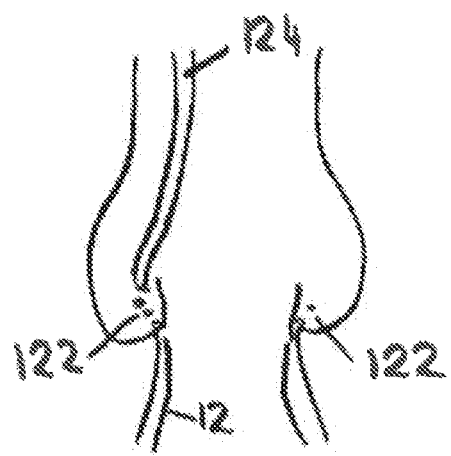
FIG. 15 is a schematic drawing illustrating administration of a sealant around the stent-valve, according to some embodiments of the disclosure.

FIG. 15 illustrates an alternative seal arrangement in which a sealant 122 is dispensed from the delivery catheter 124 (or from a further delivery catheter inserted after implantation), in order to seal around the periphery of the stent valve 10. For example, the sealant is dispensed on the outflow side of the stent-valve to seal any gaps between the upper crown and the native leaflets.

Figure 16:
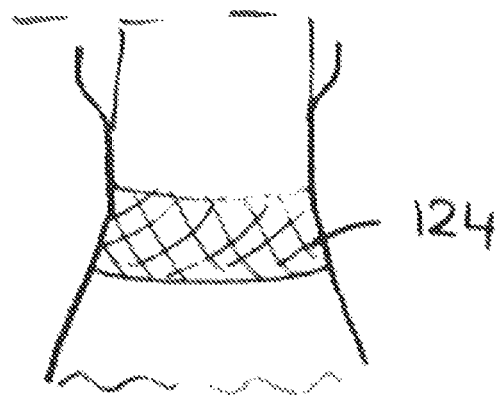
FIG. 16 is a schematic view of an alternative sealing arrangement using coagulation material, according to some embodiments of the disclosure.

FIG. 16 illustrates an alternative seal arrangement comprising material 124 that provides hemostatic and/or coagulant effects in response to contact with blood. The material 124 may, for example, be carried by, or impregnated or otherwise embodied within the outer skirt. The material may be captive within a containing chamber, for example a flexible and/or distensible pouch or cuff. The combination of inner and outer skirts, with one comprising such material, can provide an especially effective seal arrangement.

Figure 17:
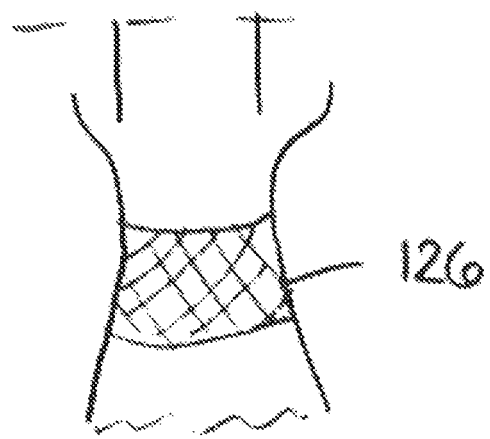
FIG. 17 is a schematic view of an alternative sealing arrangement using material that elutes calcium locally, according to some embodiments of the disclosure.

FIG. 17 illustrates an alternative seal arrangement comprising material 126 that elutes calcium locally. The calcium may deposit directly or indirectly against the surrounding tissue/lumen such that any gaps can be occluded. The material 126 may, for example, be carried by, or impregnated or otherwise embodied within the outer skirt. The material may be captive within a containing chamber, for example a flexible and/or distensible pouch or cuff. The combination of inner and outer skirts, with one comprising such material, can provide an especially effective seal arrangement.

Although the seal arrangements have been described as alternatives, it is envisaged that any two or more of the seal arrangements may be combined for synergistic effect.

Any and all references to publications or other documents, including but not limited to, patents, patent applications, articles, webpages, books, etc., presented in the present application, are herein incorporated by reference in their entirety.

Although a few variations of the disclosed subject matter have been described in detail above, other modifications are possible. For example, any logic flow depicted in the accompanying figures and/or described herein does not require the particular order shown, or sequential order, to achieve desirable results. Other implementations may be within the scope of at least some of the following exemplary claims.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to stent-valves, and/or seals for stent-valves. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure).

What is claimed:

1. A stent-valve for transcatheter implantation to replace a cardiac valve, the stent-valve being compressible to a compressed state for delivery, and expandable to an operative state for implantation, the stent-valve comprising a stent, a plurality of leaflets for defining a prosthetic valve, a paravalve seal for sealing against surrounding tissue, and a seal support, wherein the paravalve seal comprises a skirt, the skirt including an inner skirt disposed on an interior of the stent and an outer skirt disposed on an exterior of the stent, the inner skirt and outer skirt together defining a one or more pocket, wherein the outer skirt or portions thereof is biased radially outwardly to distend away from the body of the stent such that each pocket defines an open mouth facing towards an outlet end of the stent, and an end of the pocket opposite the mouth is closed, wherein the seal support comprises a plurality of cantilever elements fixed directly to the stent and biased radially outward from the stent and holding the mouth of the pocket open and radially outward away from the body of the stent, wherein the seal is configured such that blood flow in a reverse direction biases the seal pocket in an open state to obstruct such flow.

2. The stent-valve of claim 1, wherein each of the cantilever elements comprises a single strut or plural struts.

3. The stent-valve of claim 2, wherein each of the cantilever elements is associated with a respective aperture of a lattice structure of the stent.

4. The stent-valve of claim 3, wherein each of the cantilever elements has one end coupled directly to or integral with the stent body, and an opposite or remote end that is free to deploy outwardly.

5. The stent-valve of claim 4, wherein the cantilever elements extend generally in the same direction as each other, or, where the cantilever elements are arranged in two opposite directions or in a variety of different directions.

6. The stent-valve of claim 5, wherein the pocket is pushed outwardly by the cantilever elements.

7. The stent-valve of claim 6, wherein the pocket is positioned such that back-pressure of blood, or para-valvular blood flow in the reverse direction from outlet to inlet end of the stent, fills the pocket to cause the pocket to further to distend, thereby enhancing the seal effect to obstruct paravalvular flow.

8. The stent-valve of claim 7, wherein the seal support at least partly biases the skirt outwardly into engagement with surrounding tissue.

9. The stent-valve of claim 1, wherein the seal support is defined by an upper crown of the stent.

10. The stent-valve of claim 9, wherein the skirt is attached to the upper crown.

11. The stent-valve of claim 10, wherein the cantilever elements are independently deformable for conforming to local anatomy.

12. The stent-valve of claim 1, wherein one wall of each pocket is defined by a portion of the outer skirt and another wall of each pocket is defined by a portion of the inner skirt.

13. The stent-valve of claim 1, wherein each pocket is associated with a respective aperture of a lattice structure of the stent.

14. The stent-valve of claim 1, wherein a portion of the stent extends beyond the pocket towards both an inflow end and an outflow end of the stent-valve.

15. A stent-valve for transcatheter implantation to replace a cardiac valve, the stent-valve being compressible to a compressed state for delivery and expandable to an operative state for implantation, the stent-valve comprising:
  a stent;
  a plurality of leaflets for defining a prosthetic valve; and
  a seal for sealing against surrounding tissue, the seal including an inner skirt disposed on an interior of the stent, an outer skirt disposed on an exterior of the stent, and a seal support, the inner skirt and outer skirt together defining one or more pocket, wherein a portion of the stent extends beyond the pocket towards both an inflow end and an outflow end of the stent-valve, wherein a portion of the outer skirt defining each pocket is biased radially outwardly to distend away from the body of the stent such that each pocket defines an open mouth facing towards the outflow end of the stent, and an end of the pocket opposite the mouth in the direction towards the inflow end of the stent is closed, wherein the seal support comprises a plurality of cantilever elements fixed directly to the stent and biased radially outward from the stent and holding the mouth of the pocket open and radially outward away from the body of the stent, wherein the seal is configured such that blood flow in a reverse direction from the outlet to the inlet biases the seal pocket to a deployed in an open state to obstruct such flow.

16. The stent-valve of claim 15, wherein one wall of each pocket is defined by a portion of the outer skirt and another wall of each pocket is defined by a portion of the inner skirt.

17. The stent-valve of claim 15, wherein each pocket is associated with a respective aperture of a lattice structure of the stent.

* * * * *